(12) United States Patent
Tsuchiya et al.

(10) Patent No.: US 6,194,157 B1
(45) Date of Patent: Feb. 27, 2001

(54) METHOD FOR SEPARATING BIOLOGICAL SUBSTANCES BY USING PHOTORESIST

(75) Inventors: Hiroshi Tsuchiya; Yoshiaki Tachiiri; Toshiaki Ito, all of Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 0 days.

(21) Appl. No.: 09/355,482

(22) PCT Filed: Feb. 3, 1998

(86) PCT No.: PCT/JP98/00438

§ 371 Date: Jul. 30, 1999

§ 102(e) Date: Jul. 30, 1999

(87) PCT Pub. No.: WO98/33902

PCT Pub. Date: Aug. 6, 1998

(30) Foreign Application Priority Data

Feb. 3, 1997 (JP) .................................................. 9-034321

(51) Int. Cl.$^7$ .............................. C12Q 1/68; C08G 73/00; C08G 283/00; C08G 63/00; C08H 5/04
(52) U.S. Cl. .............................. 435/6; 528/422; 528/423; 525/540; 527/312; 527/200
(58) Field of Search .................................. 528/422, 423; 525/540; 527/312, 200; 435/6

(56) References Cited

U.S. PATENT DOCUMENTS 5,770,685 * 6/1998 Stebani et al. ........................ 528/422
6,087,134 * 7/2000 Saunders .............................. 435/91.2

OTHER PUBLICATIONS

Flounders et al., "Patterning of immobolized antibody layers via photolithography and oxygen plasma exposure", Biosensors and Bioelectronics, vol. 12 (6), pp. 447–456, 1997.*

S. Noguchi, et al., Clonal Analysis of Predominantly Intraductal Carcinoma and Precancerous Lesions of the Breast by Means of Polymerase Chain Reaction, Cancer Research, vo. 54, pp. 1849–1853, Apr. 1994.

Z. Zhuang, et al., A Microdissection Technique for Archival DNA Analysis of Specific Cell Populations in Lesions <1mm in Size, American Journal of Pathology, vol. 146, No. 3, pp. 620–625. Mar. 1995.

E. Kawasaki, Sample Preparation From Blood, Cells, And Other Fluids, PCR Protocols: A Guide to Methods and Applications, pp. 146–152, 1990.

S. Hadano et al., Laser Microdissection and Single Unique Primer PCR Allow Generation of Regional Chromosome DNA Clones from a Single Human Chromosome, Genomics, vol. 11, pp. 364–373, 1991.

E. E. Karrer et al., In situ isolation of mRNA from individual plant cells: creation of cell–specific cDNA libraries, Proc. Natl. Acad. Sci., vol. 92, No. 9, pp. 3814–3818, Apr. 1995.

J. Eberwine et al., Analysis of gene expression in single live neurons, Proc. Natl. Acad. Sci., vol. 89, No. 7, pp. 3010–3014, Apr. 1992.

* cited by examiner

*Primary Examiner*—Jeffrey Fredman
*Assistant Examiner*—Arun Chakrabarti
(74) *Attorney, Agent, or Firm*—Oliff & Berridge, PLC

(57) ABSTRACT

After a photoresist (2) is used to fix a biological sample, in order to obtain a particular biological substance, for example, a certain cell or biopolymer, from the biological sample embedded in the photoresist (2), properties of the photoresist are changed by exposing the portion of the photoresist (2) that covers the biological substance to light L which has an appropriate wavelength. The biological substance embedded in the changed photoresist is collected.

22 Claims, 5 Drawing Sheets

METHOD FOR SEPARATING BIOLOGICAL SUBSTANCES BY USING PHOTORESIST

TECHNICAL FIELD

The present invention relates to a method for separating a target biological substance.

BACKGROUND ART

The following technologies have been reported as methods for extracting DNA or RNA from a particular single cell or a clump of cells, or from tissue or a portion of tissue.

(1) In one method, a certain portion of cells, a tissue, or a chromosome is cut away using a micro needle while viewed under a microscope. DNA or RNA is extracted from the removed portion. (by S. Noguchi, et al in Cancer Research 54, p1849–1853, 1994 and by Z. Zhuang, et al in American Journal of Pathology vol. 146, No. 3, p620–625)

(2) In another method, a certain cell or tissue is pierced with a micro capillary tube while viewed under a microscope and the contents of the certain cell or tissue are withdrawn through the micro capillary tube. (Proc. Natl. Acad. Sci. USA Vol. 92, p3814–3818, 1995 and in Proc. Natl. Acad. Sci. USA Vol. 89, p3010–3014, 1992)

(3) In a further method, a laser is used to burn off portions other than a target cell or tissue. Afterward, the target cell or tissue is collected and DNA or RNA is extracted from the collected cell or tissue. (Genomics vol. 11, p364–373, 1991)

However, the method using the micro capillary tube requires accurate manipulation of the micro capillary tube under a microscope and so requires a highly-skilled and experienced technician. For this reason, it is difficult to collect the contents of the target cell or tissue only without contamination. Also, although easier manipulation can be anticipated with the method using a laser, it is difficult to completely burn away portions other than the target cell or tissue using a laser. As a result, it is difficult to avoid contamination of the target cell or tissue from surrounding material. For this reason, when DNA or RNA is extracted using the above-described methods and afterward amplified, the contamination will result in an undesirably high background.

It is a purpose of the present invention to provide a simple method for easily separating biological substances, such as certain cells, tissues, biopolymers or low weight biomolecules, for example, biomolecules such as DNA, RNA, protein, or glucose, with little impurities.

DISCLOSURE OF INVENTION

In order to attain the above-described objective, the present invention is characterized by using a photoresist to separate biological substances.

The present invention is also characterized by embedding or encasing a biological sample, such as a cell or a tissue, in photoresist.

Photoresist is a photosensitive resin that is widely used in the production of transistors and integrated circuits.

The present invention provides a method characterized by first fixing a biological sample using a photoresist. Afterward, in order to retrieve a particular biological substance, such as a target cell, biopolymer, or low weight biomolecule, from the biological sample embedded in the photoresist, either the portion of the photoresist covering the biological substance, or all other portions of the photoresist, are selectively exposed to light such as a visible light, ultraviolet light, X-rays, or an electron beam, thereby differentiating the characters of the exposed and unexposed portions of the photoresist. The biological substance embedded in the photoresist is then collected.

According to another aspect, the present invention provides a method characterized by first fixing a biological sample using a positive type photoresist. Afterward, in order to retrieve a particular biological substance, such as a target cell, biopolymer, or low weight biomolecule, from the biological sample embedded in the photoresist, the portion of the photoresist covering the biological substance is exposed to light such as visible light, ultraviolet light, X-rays, or an electron beam, thereby decomposing the photoresist or changing properties of the photoresist (sometimes referred to collectively as "changing properties of the photoresist," hereinafter). Then, the biological substance embedded in the changed photoresist is collected.

According to still another aspect, the present invention provides a method characterized by first fixing a biological sample using an amphoteric type photoresist. Afterward, in order to retrieve a particular biological substance, such as a target cell, biopolymer, or low weight biomolecule, embedded in the photoresist, a region of the photoresist other than its portion covering the biological substance is exposed to light such as visible light, ultraviolet light, X-rays, or an electron beam, thereby differentiating solubility of the exposed portion of the photoresist with respect to a solvent from solubility of the unexposed portion of the photoresist with respect to the solvent. Next, the exposed photoresist portion and the portion of the biological sample embedded in the exposed photoresist portion are removed based on the difference in solubility. Afterward, the remaining unexposed portion of the photoresist is dissolved in another appropriate solvent and the biological substance embedded in the unexposed portion is collected.

According to still another aspect, the present invention provides a method characterized by first covering a biological sample with a negative type photoresist. Afterward, the biological sample is fixed by solidifying the photoresist (using solvent casting method). Afterward, in order to retrieve a particular biological substance, such as a target cell, biopolymer, or low weight biomolecule, a region of the photoresist other than the portion covering the biological substance is exposed to light such as visible light, ultraviolet light, X-rays, or an electron beam, thereby making the exposed photoresist portion insoluble with respect to a solvent. Next, the biological substance, which is covered in the portion of the photoresist that is not made insoluble with respect to the solvent, is collected.

Thus, the present invention is characterized by using a photoresist for separating a target biological substance.

That is, according to one aspect, the present invention provides a method for separating a biological substance, the method comprising the steps of:

(a) covering, with a photoresist, a biological sample that includes a biological substance;

(b) fixing the biological sample by solidifying the photoresist;

(c) selectively exposing the solidified photoresist to light either at a portion that covers the biological substance or at another portion; and (d) selectively dissolving, using a solvent, at least one of the portion of the photoresist that is exposed to light during the step (c) and the portion that is not exposed to light, and collecting the biological substance embedded in the photoresist.

No particular limitations are placed on the photoresist used in the present invention. That is, a positive type photoresist, an amphoteric type photoresist, or a negative type photoresist could be used.

A positive type photoresist is a photoresist having a character wherein portions exposed to light become soluble with respect to a solvent.

According to another aspect, therefore, the present invention provides a method for separating a biological substance, the method comprising the steps of:

(a) covering, with a positive type photoresist, a biological sample that includes a biological substance;

(b) fixing the biological sample by solidifying the photoresist (a solvent casting method);

(c) exposing the solidified photoresist to light at a portion that covers the biological substance; and (d) dissolving, using a solvent, the portion of the photoresist that is exposed to light during the step (c), and collecting the biological substance embedded in the photoresist.

A negative type photoresist is a photoresist having a character wherein portions exposed to light become insoluble with respect to a solvent.

Accordingly, in still another aspect, the present invention provides a method for separating a biological substance, the method comprising the steps of:

(a) covering, with a negative type photoresist, a biological sample that includes a biological substance;

(b) fixing the biological sample by solidifying the photoresist (a solvent casting method);

(c) exposing, to light, a portion of the photoresist that covers a region other than a portion of the biological sample including the biological substance to be collected, thereby making the photoresist at the exposed portion insoluble with respect to a solvent; and (d) collecting the biological substance covered by the unexposed portion of the photoresist, which is not made insoluble with respect to the solvent.

An amphoteric type photoresist is a photoresist having a character wherein characteristics of either positive or negative photoresists can be obtained depending on selection of solvent to be applied after its exposure to light. In other words, the amphoteric type photoresist is a photoresist having a character wherein exposed and unexposed portions present different solubilities with respect to a solvent.

Accordingly, in a further aspect, the present invention provides a method for separating a biological substance, the method comprising the steps of:

(a) covering, with an amphoteric type photoresist, a biological sample that includes a biological substance;

(b) fixing the biological sample by solidifying the photoresist (a solvent casting process);

(c) exposing, to light, a portion of the photoresist that covers a region other than a portion of the biological sample including the biological substance to be collected, thereby producing a difference in solubility with respect to a solvent between the exposed portion of the photoresist and the unexposed portion of the photoresist; and (d) collecting the biological substance embedded in the unexposed portion of the photoresist, based on the difference obtained by the process (c) in solubility with respect to the solvent between the exposed portion of the photoresist and the unexposed portion of the photoresist.

BEST MODE FOR CARRYING OUT THE INVENTION

Figure 1:
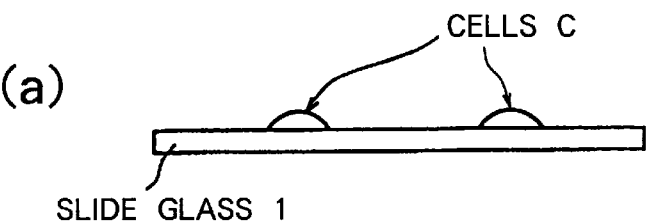
FIGS. 1(a) to 1(e) schematically show processes in a first example of the present invention.
Figure 1:
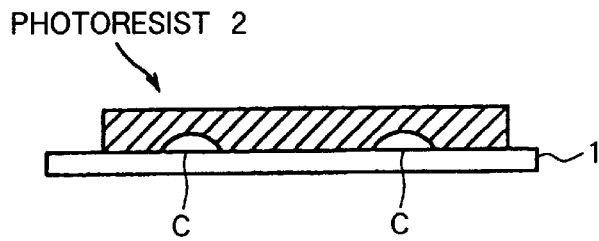
Figure 1:
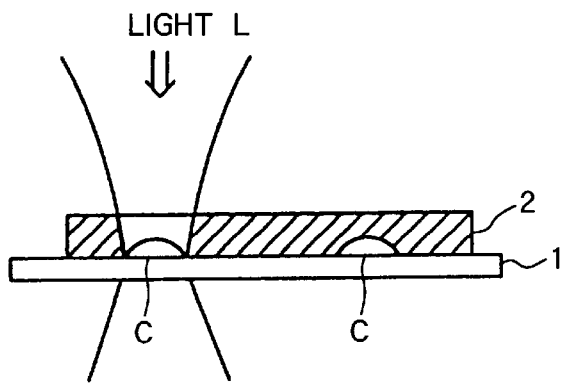
Figure 1:
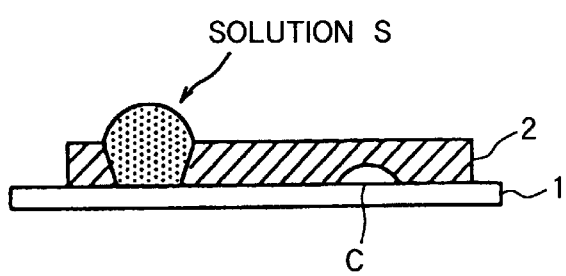
Figure 1:
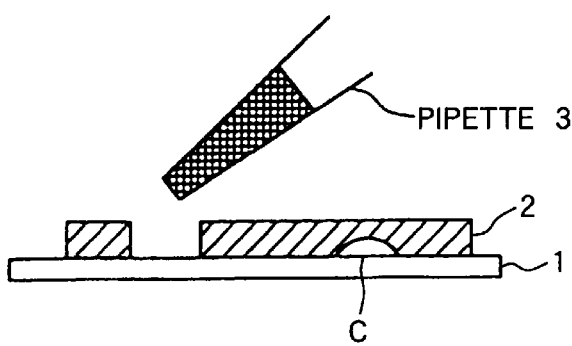

The best mode for carrying out the method of the present invention will be described below.

(1) Biological Samples

No particular limits are placed on what biological samples can be used as the subject of the method of the present invention. Examples of biological samples that can be used with the present invention include: tissue or tissue sections, such as brains, livers or sections thereof; cells; biopolymers, such as proteins, peptides, nucleic acid, and various physiological active substance; and low weight biomolecules like glucose and hormones.

In order to use a tissue, the tissue is extracted from a living organism. A section of the tissue can be prepared and used, or the tissue can be broken up in a homogenizer, for example, and the homogenate can be used.

There are no particular limitations on which types of cells can be used with the present invention. Examples of those cells, to which the present invention can be applied, include: adhesive cells, such as fibroblast and epithelial cells; and suspension cells, such as blood cells and certain types of cancer cells. The present invention can be applied satisfactorily to those cells regardless of whether they are taken from a living body or are cellulined cultured cells.

The present invention can be applied also to materials retrieved from living organisms, to extracts from cells or tissues, or to refined portions of biological substances. Examples of materials retrieved from living organisms include blood, amniotic fluid, feces, and urine.

(2) Processes for Separating Biological Substances Using Photoresist

A positive type photoresist, an amphoteric type photoresist, or a negative type photoresist can be used in the separation method of the present invention. Explanations will therefore be provided for when a positive type photoresist is used, for when an amphoteric type photoresist is used, and for when a negative type photoresist is used.

(I) Method using Positive Photoresist

According to an embodiment of the present invention, a positive type photoresist is used. That is, a biological sample is embedded in a positive photoresist. Then, only a portion of the photoresist that covers a target portion of the biological sample is exposed to light, such as visible light, ultraviolet light, X-rays, or an electron beam, to make the exposed portion of the photoresist soluble in a solvent. The portion of the biological sample embedded in the exposed portion of the photoresist is collected.

(I-1) Method of Preparing Biological Samples Embedded in Positive Type Photoresist The method of the present invention is characterized by encasing or embedding the biological sample in photoresist. The method of encasing the biological sample can be selected as appropriate for the biological sample used.

The following text describes, in more detail, a method of preparing a biological sample and then encasing the biological sample in photoresist, both for the case where suspension cells are used and for the case where a section of a tissue is used. However, the embodiment of the present invention is not limited to the examples described below.

1) Method of Encasing Cell Suspension in Photoresist

After suspension culture in an appropriate medium, the cells are collected with a centrifuge, and then resuspended in an appropriate solution. Afterward, the suspension including the appropriate number of cells is mixed at an appropriate ratio with a photoresist dissolved or suspended in an appropriate solvent or water-based medium. The mixture ratio of the photoresist composition to the cell suspension should be selected as appropriate for the type of the photoresist composition used, but is not particularly important as long as the photoresist can be sufficiently solidified during subsequent operations. For example, the photoresist composition and the cell suspension can be mixed in a ratio of between 20:1 and 5:1, and more desirably, between 10:1 and 8:1. The suspension liquid is spread on a solid support, such as a slide glass or a plastic plate, and left to sit for a predetermined duration of time at a predetermined temperature until the photoresist solidifies.

2) Method of Encasing a Tissue Section Using Positive Type Photoresist

A target tissue, such as a brain or a liver, is extracted from a living organism. An ultra thin section, having a thickness of several micrometers, is prepared from the target tissue using paraffin encasing techniques or freezing techniques. The section prepared by freezing techniques is spread on a solid support such as a slide glass. Afterward, photoresist composition is spread so as to cover the tissue section. Next, the photoresist is solidified by leaving the photoresist for a certain duration of time, at a certain temperature.

The positive type photoresist used in the present invention can be any positive type photoresist without any particular limitations as long as it can be solidified in a form encasing the biological sample therein and as long as it is a photodegradation type photoresist or a photoinduced chemical property changing photoresist, wherein the photodegradation type photoresist breaks down or decomposes when exposed to light, such as visible light, ultraviolet light, X-rays, or electron beams, and the photoinduced chemical property changing type photoresist changes its properties when exposed to light, such as visible light, ultraviolet light, X-rays, or electron beams. That is, the photoinduced chemical property changing type photoresist, such as a mixture of a o-naphthoquinone azide derivative and a phenol novolac resin, can be used as one example of the positive photoresist. The photodegradation type photoresist including polymethylmethacrylate as its main ingredient can be used as another example of the positive type photoresist.

According to the present invention, the positive photoresist can be solidified by leaving it to sit for a certain duration of time at a certain temperature. The duration of time and the temperature can be selected as appropriate for the solvent or water-based medium in the positive photoresist composition and for the biological sample to be collected. Generally, photoresist is solidified by applying heat to the photoresist. For example, photoresist is solidified by heating it between room temperature and 100° C. It is desirable that the photoresist be solidified by heating it to between 80° C. and 100° C. for one to several minutes or to between 30° C. and 60° C. for ten plus several minutes to several hours. For example, if the objective is to collect DNA or RNA using the method of the present invention, a condition solidifying the positive type photoresist by heating it to about 95° C. for one to a few minutes can be selected. When the biological sample to be fixed can be damaged by heating, it is desirable to solidify the photoresist at room temperature or lower, for example, to only a few degrees centigrade. In this case, acetone or other solvent that tends to vaporize at low temperatures can be used as the solvent of a normally used photoresist composition. Further, the photoresist can be solidified by keeping it under a low pressure to promote evaporation of the solvent. The photoresist can be selected according to the purpose.

When the properties of the positive type photoresist are changed by exposing the positive type photoresist to light such as visible light, ultraviolet light, X-rays, or an electron beam, change of its properties can be controlled by regulating the wavelength and intensity of the light.

The positive type photoresist used in the method of the present invention can be used either dissolved in an organic solvent or as an emulsion by further addition of water. The emulsified photoresist can be used in situations when problems would arise if the target biological sample were mixed with a highly concentrated organic solvent. Commercially available positive type photoresist can be used satisfactorily with the present invention. Because commercially available photoresist is generally dissolved in organic solvent, when it is desirable that the photoresist be an emulsion type photoresist composition, water can be added to the commercially available photoresist and the result used as an emulsion. When the concentration of the commercial photoresist is higher than desired, the photoresist can be diluted using an appropriate solvent or a water based medium, such as ethyl lactate.

According to the present invention, no particular limitations are set for the solid support used for fixing the biological sample. For example, a slide glass or plastic plate could be used. The solid support can be selected as appropriate for the biological sample, the photoresist, and the fixing conditions. It is desirable to use a slide glass when the photoresist is to be solidified at a relatively high temperature.

A biological sample embedded in the positive type photoresist as described above according to the present invention can be preserved in this condition in the positive type photoresist.

(I-2) Collecting Target Biological Sample, Low Weight Biomolecule, or Biopolymer The cell or tissue fixed in the photoresist using the above-described method can be observed by phase contrast or differential interference microscopy. Thus, the biological tissue embedded in the photoresist obtained according to the present invention can be observed, using the optical microscope, in the embedded condition and so is easy to manipulate afterwards.

Further, when the cell or tissue is stained by fluorescent dyes using in situ hybridization or immunofluorescent techniques and then the biological tissue is embedded in a photoresist using the method of the present invention, the target position can be specified by irradiating the embedded cell or tissue with light of an excitation wavelength for the florescent dyes. In this case, to prevent the photoresist from optically reacting to the excitation light, it is necessary to select the florescent dyes and the photoresist so that the wavelength of the excitation light be longer than the wavelength of light used to expose the photoresist.

After the target portion is specified using the above-described method, the photoresist covering the target portion is exposed to light to change its properties. Either normal light or laser light can be used as the light for changing properties of the photoresist. A high pressure mercury lamp or xenon lamp can be used as the light source when the region of the photoresist that covers the biological substance to be collected and that is to have its properties changed is relatively large. In this case, a fluorescent microscope that is provided with the lamp can be used as is. When the region of the collection target is relatively small, it is possible to change properties of the photoresist only at its extremely narrow region using a laser light. Further, a laser processing device or a laser microscope provided with a scanning device can be used when it is desirable to change properties of the photoresist, which covers a cell or tissue, in a particular shape such as a particular pattern.

According to the present invention, visible light, ultraviolet light, deep ultraviolet light, an electron beam, X-rays, an ion beam, or the like can be used as light for changing properties of the photoresist.

The wavelength of light used to change properties of the positive type photoresist can be appropriately selected according to the photoresist used. Further, when irradiating the embedded biological sample with particular wavelength light will undesirably affect the biological sample, such undesirable effects can be prevented by selecting an appropriate combination of photoresist and wavelength of the exposure light.

The method according to the present invention has no particular limitations on methods for removing the changed photoresist portion and recovering target biological samples. For example, such an appropriate solvent or solution as buffer can be dripped onto the decomposed photoresist portion and the target material retrieved with the solvent or solution. When the changed photoresist is soluble in a weak alkaline solution, the target biological substance can be retrieved by dissolving the photoresist using the weak alkaline solution.

It is possible to remove only the changed photoresist in cases when the biological sample has a strong tendency to adhere to the solid support. In this case, the biological sample including the target biological substance can be retrieved while supported on the solid support and can be used in this condition for a variety of purposes.

The solvent used for collection can be selected as appropriate for the nature of the changed photoresist, the biological substance to be collected, and the intended use of the biological substance. For example, a weak alkaline solvent can be used when the above-described mixture of a o-naphthoquinone azide derivative and a phenol novolac resin is used as the resist and DNA embedded in the mixture is the target to be collected. In this case, the changed photoresist is dissolved in the weak alkaline solvent.

The solution collected using the method of the present invention can be treated in a variety of optional ways depending on the purpose of the user. For example, after solution including a target DNA is obtained using the method of the present invention, the DNA can be isolated by ethanol precipitation and proteinase K treatment.

The biological samples, biopolymers, or low weight biomolecules retrieved using the method of the present invention can be used as a biological substance for a variety of purposes. For example, when the method of the present invention is used for retrieving DNA or RNA, the retrieved particular DNA or RNA can be used for gene cloning, for preparing a cDNA library, for identifying a gene based on PCR techniques, or for genetic diagnosis. When the method of the present invention is used to retrieve a protein, the retrieved protein can be used in amino acid sequencing and the like. When the method of the present invention is used to retrieve low weight biomolecules such as glucose and hormones, the retrieved low weight biomolecules can be used in biochemical diagnoses.

(II) Method Using Amphoteric Type Photoresist

According to another embodiment of the present invention, an amphoteric type photoresist is used. That is, a biological sample is embedded in an amphoteric type photoresist. The photoresist is then exposed to light at its portion that covers regions other than the portion of the biological sample that includes the target biological substance and that is to be collected. As a result, solubility of the photoresist with respect to a solvent will differ at exposed and unexposed portions. Next, by utilizing this difference in solubility, the biological substance embedded in the unexposed portion of the photoresist is collected.

An amphoteric type photoresist is a photoresist having a character wherein characteristics of either positive or negative photoresists can be obtained depending on selection of solvent to be applied after its exposure to light. Accordingly, the amphoteric type photoresist has solubility, with respect to a solvent, that differs for exposed and unexposed portions. By utilizing the nature of the amphoteric photoresist, unneeded photoresist portion can be removed using the solvent and the remaining portion of photoresist can be collected using another solvent. Accordingly, in the method using the amphoteric photoresist, the process of collecting is comprised from an operation for removing unneeded portions during an initial development and a next operation for collecting required portions during a subsequent development procedure. That is, the process of collecting employs a two-step collection method that includes the operation of removing unneeded portions before the operation of collecting required portions.

That is, the collection process includes a removal step and a collection step. During the removal step, based on the difference in solubility, only the exposed portion of the photoresist is dissolved and the biological sample portion embedded in the exposed portion of the photoresist is removed. During the collection step, the remaining unexposed portion of the photoresist is dissolved using a different solvent and the biological substance embedded in the unexposed portion of the photoresist is collected.

(II-1) Method of Preparing Biological Sample Embedded in Amphoteric Photoresist

The amphoteric photoresist used in this embodiment of the present invention can be any amphoteric photoresist without particular limitations as long as it can solidify in a form that embeds the biological sample therein and as long as it has a difference, in solubility with respect to a solvent, in portions exposed and not exposed by light. For example, photoinduced chemical property changing type photoresist of a type that includes a material generating acid as catalyst by exposure to light and that exhibits properties causing hydrolysis of resist material by exposure to light can be used as the amphoteric photoresist. When a mixture of poly (p-tert-butoxl carbonyl oxystyrene) and onium salt is used as an example of the photoinduced chemical property changing type photoresist, exposed portions will be soluble in an alkaline solution, but insoluble in a small polarity solvent like hexane. On the other hand, unexposed portions will be insoluble in an alkaline solution, but soluble in a small polarity solvent like hexane.

The method of encasing the biological sample in an amphoteric photoresist, according to the present invention, is the same as that described above for encasing the biological sample in a positive photoresist.

According to the present invention, the amphoteric photoresist can be solidified by leaving it to sit for a certain duration of time at a certain temperature. When the photoresist is solidified by leaving it to sit for the certain duration of time at the certain temperature, the duration of time and the temperature can be selected as appropriate for the solvent or water-based medium in the amphoteric photoresist composition. Generally, photoresist is solidified by applying heat to the photoresist. For example, photoresist is solidified by heating the photoresist between room temperature and 100° C. It is desirable that the photoresist be solidified by heating it to between 80° C. and 100° C. for one to several minutes or to between 30° C. and 60° C. for ten plus several minutes to several hours. For example, if the objective is to collect DNA or RNA using the method of the present invention, the photoresist can be solidified by heating the photoresist to about 95° C. for one to a few minutes. When the biological sample to be fixed can be damaged by heating, it is desirable to use a photoresist that can be solidified at room temperature or lower, for example, at a few degrees centigrade. The photoresist can be selected according to the objective.

When the properties of the amphoteric photoresist are changed by exposing the amphoteric photoresist to light, change in properties of the photoresist can be controlled by regulating the wavelength and intensity of the light.

The amphoteric photoresist used in the method of the present invention can be used either dissolved in an organic solvent or as an emulsion by further addition of water. The emulsion type photoresist can be used in situations when problems would arise if the target biological sample were mixed with a highly concentrated organic solvent.

Also in the embodiment where the amphoteric photoresist is used, no particular limitations are set for the solid support used for fixing the biological sample. For example, a slide glass or plastic plate could be used.

A biological sample embedded in the amphoteric photoresist as described above according to the present invention can be preserved in this condition in the amphoteric photoresist.

(III-2) Collecting Target Biological Sample, Low Weight Biomolecule, or Biopolymer Similarly to the case where the positive photoresist is used, the cell or tissue fixed in the amphoteric photoresist using the above-described method can be observed in the embedded condition, with an optical microscope, using phase contrast or differential interference techniques.

Further, the cell or tissue can be stained with fluorescent dyes, similarly to the case where the positive photoresist is used.

Visible light, ultraviolet light, deep ultraviolet light, an electron beam, X-rays, an ion beam, or the like can be used as light for changing properties of the amphoteric photoresist. The wavelength of light used to change properties of the amphoteric photoresist can be appropriately selected according to the photoresist used. Further, when irradiating the embedded biological sample with particular wavelength light will undesirably affect the biological sample, such undesirable effects can be prevented by selecting an appropriate combination of photoresist and wavelength of the exposure light.

According to the present embodiment, based on the difference in solubility of the exposed and unexposed portions of the photoresist to a solvent, the exposed portion of the photoresist and the portion of the biological sample embedded in the exposed portion of the photoresist are removed and, afterward, the portion of the biological sample embedded in the unexposed portion of the photoresist is collected. The solvent used in the collection can be selected as appropriate for the photoresist used and for the target biological substance to be collected.

For example, when a mixture of a o-naphthoquinone azide derivative and a phenol novolac resin is used as the amphoteric photoresist, the character of the photoresist will be that exposed portions are soluble in organic solvents and weak alkaline solutions, but the unexposed portions are soluble in organic solvents and insoluble in weak alkaline solutions. To utilize this difference in solubility, first, the solidified photoresist is exposed to light at portions other than those covering the portion of the biological sample that includes the target biological substance to be collected. Next, the weak alkaline solution is used to remove the portion of the biological sample embedded in the exposed portion of the photoresist. Afterward, the remaining unexposed portion of the photoresist and the portion of the biological sample covered by the unexposed portion of the photoresist are dissolved using an organic solvent such as xylene, and the target biological substance is collected.

Next, the recovered biological substance can be used for a variety of objectives, such as genetic cloning.

(III) Method Using Negative Type Photoresist

According to still another embodiment of the present invention, a negative type photoresist is used. That is, the biological sample is covered with a negative type photoresist. Then, the biological sample is fixed by solidifying the negative type photoresist. Afterward, the photoresist is exposed to light at regions other than those covering the portion of the biological sample that includes a target biological substance and that is to be collected. As a result of this exposure, the exposed region of the photoresist will become insoluble to a solvent. Afterward, the biological substance covered by the unexposed portion of the photoresist, which has not become insoluble to the solvent, is collected.

(III-1) Method of Collecting Target Biological Substance

In the present embodiment, by exposing all regions of the photoresist other than those covering the portion of the biological sample that includes the target biological substance and that is to be collected, the exposed regions will become insoluble by a solvent.

The negative photoresist used in this embodiment of the present invention can be any negative photoresist without particular limitations as long as it becomes insoluble to a solvent when exposed to light. For example, negative photoresist such as an optical cross-linking negative photoresist or a photo polymerized resist can be used. The optical cross-linking negative photoresist generates a cross-linking reaction upon irradiation with light, X rays, or an electron beam. The photo polymerized resist contains a radical generating agent, and polymerizes when exposed to light. Vinyl cinnamate can be used as an example of the optical cross-linking negative photoresist. A mixture of methyl-methacrylate and para azide benzoic acid can be used as an example of the photo polymerized resist.

According to the present invention, a method for encasing the biological sample in a negative type photoresist is the same as described above for when a positive type photoresist or an amphoteric type photoresist is used.

According to the present invention, the negative photoresist can be solidified by leaving it to sit for a certain duration of time at a certain temperature. When the photoresist is solidified by leaving it to sit for the certain duration of time at the certain temperature, the duration of time and the temperature can be selected as appropriate for the solvent or water-based medium in the negative photoresist composition. Generally, photoresist is solidified by applying heat to the photoresist. For example, photoresist is solidified by heating the photoresist between room temperature and 100° C. It is desirable that the photoresist be solidified by heating it to between 80° C. and 100° C. for one to several minutes or to between 30° C. and 60° C. for ten plus several minutes to several hours. For example, if the objective is to collect DNA or RNA using the method of the present invention, the photoresist can be solidified by heating the photoresist to about 95° C. for one to a few minutes. When the biological sample to be fixed can be damaged by heating, it is desirable to use a photoresist that can be solidified at room temperature or lower, for example, at a few degrees centigrade. The photoresist can be selected according to the objective.

It is possible to make the photoresist insoluble with respect to a solvent by exposing the photoresist to light in a manner similar to that for the positive photoresist.

The negative photoresist used in the method of the present invention can be used either dissolved in an organic solvent or as an emulsion by further addition of water. The emulsion type photoresist can be used in situations when problems would arise if the target biological sample were mixed with a highly concentrated organic solvent.

Also in the embodiment where the negative photoresist is used, no particular limitations are set for the solid support used for fixing the biological sample. For example, a slide glass or plastic plate could be used.

A biological sample embedded in the negative photoresist as described above according to the present invention can be preserved in this condition in the negative photoresist.

According to the present embodiment, the region of the photoresist, that is to be made insoluble to a solvent by exposure to light, is determined through observation of the biological sample embedded in the photoresist, with an optical microscope, using phase contrast or differential interference techniques.

Further, the biological sample can be dyed with fluorescent coloring, similarly to the case where the positive photoresist is used.

After determining the region to be made insoluble to a solvent, the region is exposed to light.

Visible light, ultraviolet light, deep ultraviolet light, an electron beam, X-rays, an ion beam, or the like can be used as light for making the negative photoresist insoluble to a solvent. The wavelength of light used to make the negative photoresist insoluble to a solvent can be appropriately selected according to the photoresist used. Further, when irradiating the embedded biological sample with particular wavelength light will undesirably affect the biological sample, such undesirable effects can be prevented by selecting an appropriate combination of photoresist and wavelength of the exposure light.

After photoresist is exposed to light so that it becomes insoluble in the solvent, the portion of the biological sample covered by the unexposed portion of the photoresist can be collected. The solvent used in this collection process can be selected as appropriate for the photoresist used and the target biological substance to be collected.

For example, when the optical cross-linking negative photoresist such as vinyl cinnamate is used, the unexposed portion of the photoresist will be soluble in an organic solvent like xylene. Therefore, the unexposed portion of the photoresist can be collected together with the target biological substance using an organic solvent.

Biological substances, collected in the above-described manner, can be used for a variety of objectives, such as genetic cloning.

The method of the present invention will be described below in greater detail. It is noted, however, that the present invention is not limited to the following examples.

FIRST EXAMPLE

Separation Method Using Positive Photoresist (1)

A method of the first example is schematically shown in FIGS. 1(a) to 1(e).

(1-1) Fixing Cells Using Photoresist

A sterilized slide glass (76 mm×26 mm) 1 was placed in a cell cultivation Petri dish. A 20 mm×30 mm rectangular aperture was cut from the center of a 3 mm thick silicone rubber sheet, and the sheet was placed on the slide glass 1. A cell strain derived from human liver (Hu1-1) was sown in the center of the silicone rubber sheet. A DMEM culture medium (including 10% FBS) was added. The cell strain was cultured on the slide glass 1 in a single layer at 37° C. in an atmosphere of 5% $CO_2$. After cultivation, the slide glass 1 was taken out from the Petri dish, and the cells on the slide glass 1 were washed several times in PBS solution. Afterward, most of the PBS solution remaining on the slide glass 1 was removed by tilting the slide glass 1. Cells C supported on the slide glass 1 as shown in FIG. 1(a) were prepared.

After 300μ 1 of photoresist 2 (SPR6112 produced by Shipley Co.) was added onto the slide glass 1, the slide glass 1 was heated for several minutes at 95° C. to solidify the photoresist 2. The layer of the solidified photoresist 2 was approximately 7 μm thick. In this manner, the cells C were prepared embedded in the photoresist 2 as shown in FIG. 1(b). It was confirmed that the cells C can be stored in this condition for a month or more.

(1-2) Collection of Target Cell

Figure 2:
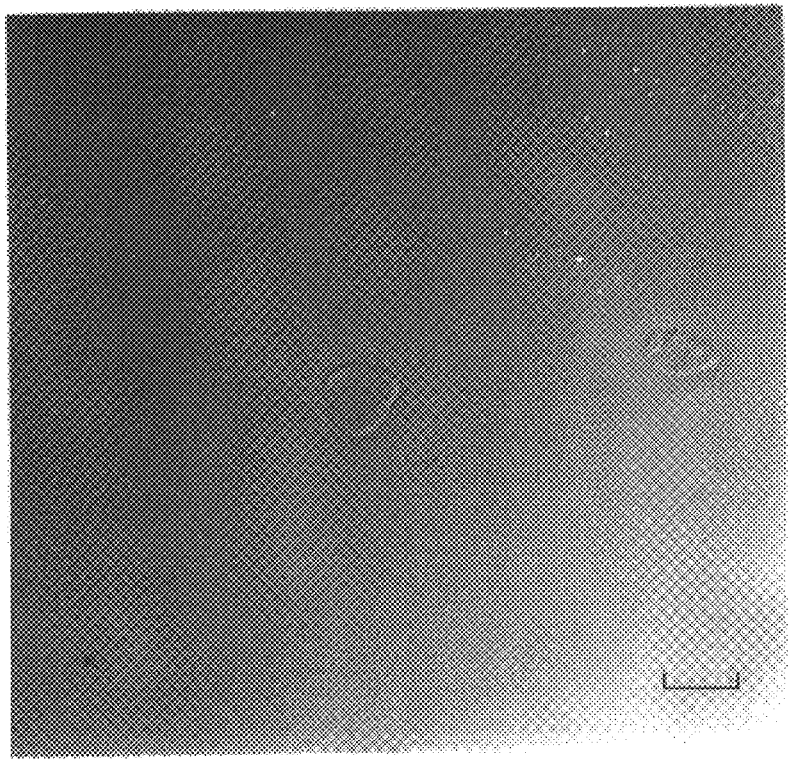
FIG. 2(a) is an image picked up through a microscope and showing the condition of cells fixed in a photoresist, wherein a scale in the drawing represents 20 $\mu$m.
FIG. 2(b) is an image picked up through a microscope and showing the condition after a target cell has been removed, wherein a scale in the drawing represents 20 $\mu$m.
Figure 2:
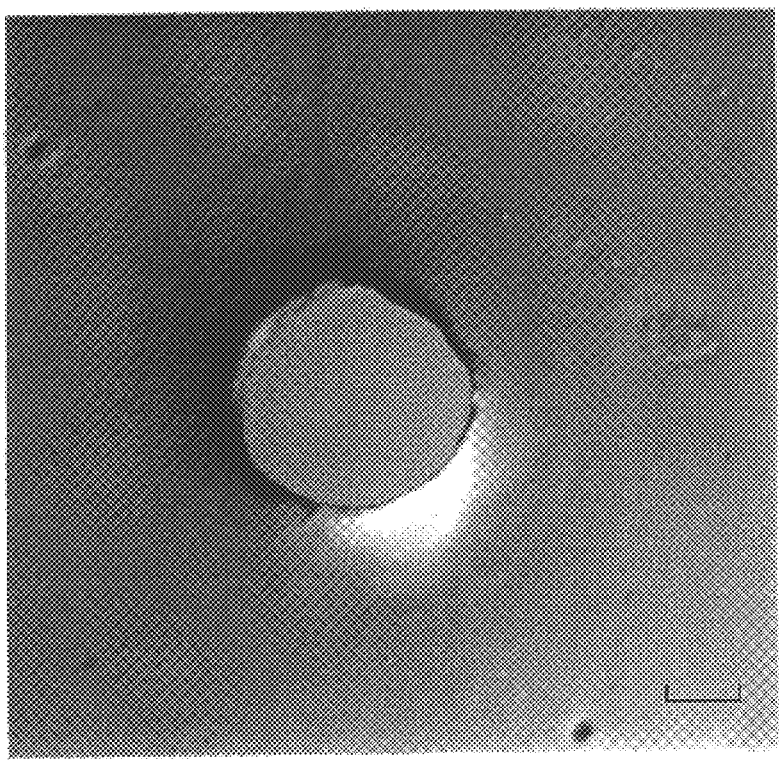

The obtained sample was transferred to under a fluorescence microscope (Axioplan model produced by Carl Zweiss) and the cells were observed using differential interference techniques. The image observed by the microscope is shown in FIG. 2(a). It can be seen from this image that two cells are separately fixed. Next, a target cell was determined. According to the present example, tests were performed with the left cell of the two observed cells as the target.

Next, as shown in FIG. 1(c), the target portion including the single target cell C was irradiated for about 10 seconds with 440 nm wavelength light L from a high pressure mercury lamp.

A solution S was prepared by adding Tween 20 to 0.1N of sodium hydroxide solution to obtain a 0.5%(v/v) concentration of Tween 20. After irradiation, about 10 μl of the solution S was added onto the irradiated portion, as shown in FIG. 1(d), and the photoresist 2 was left to sit for 8 to 10 minutes at room temperature so that the photoresist 2 was dissolved (developed). After the development was completed, as shown in FIG. 1(e), the dissolved photoresist 2 and the entire target cell C were collected using a pipette chip 3 with a soft tip in order to prevent damaging other portions of the photoresist, that is, other than the target portion. After collection, the sample was again observed under the fluorescence microscope. The image observed is shown in FIG. 2(b). It can be seen that only the target cell was cleanly removed.

The above-described operations were performed to collect the single target cell as described above, and were additionally performed to collect two target cells. That is, in addition to the experiment performed with the region including only the signal cell as the target as shown in FIGS. 2(a) and 2(b), an experiment was also performed with the region including two cells as the target.

(1-3) Extraction of DNA from Collected Cell(s) and Amplification of the DNA

The following operations were performed separately for the suspension containing the two collected target cells and for the suspension containing the single collected target cell.

Sodium hydroxide and short chains of phenol resin still exist in the suspension collected during operation (1-2). Because these materials damage activity of enzymes that are used during DNA amplification process using the PCR method, the solvent was replaced by ethanol precipitation. Explained concretely, 3M sodium acetate solution (pH 5.2) was added to the collected solution in an equal volume to the collected solution. Afterward, cold ethanol (ethanol that was cooled to −20° C.) was added in six times as much volume as the collected solution. Then, the mixture was cooled for several hours in a freezer at −20° C. Afterward, the mixture was centrifuged for one hour in a microtube centrifuge to precipitate out the DNA. Next, the wall surface and the precipitate surface of the microtube were washed in 70% ethanol and then dried to evaporate the ethanol and obtain the DNA.

Figure 3:
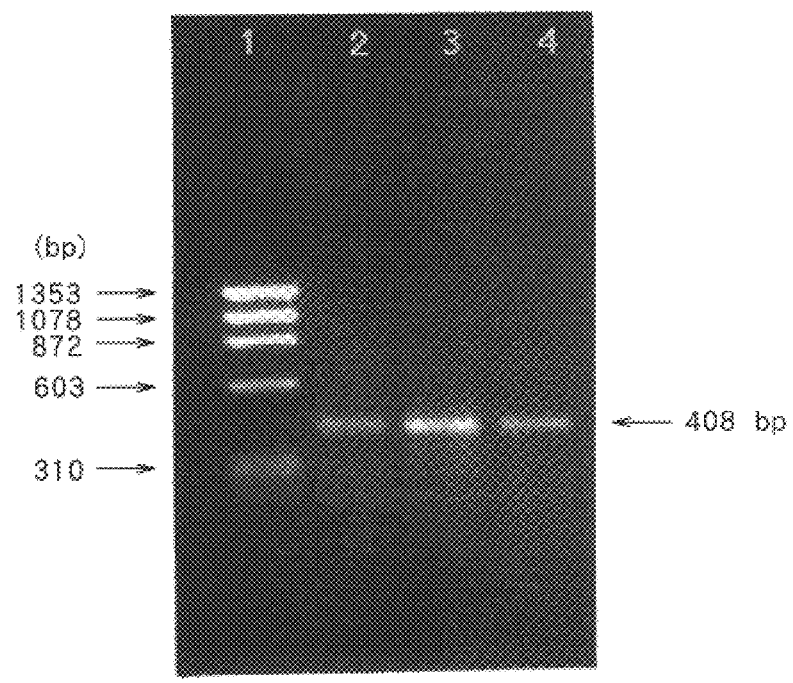
FIG. 3 is an electrophoretic pattern of PCR products obtained during a process of a first example using specific primer of human $\beta$-globulin, wherein Lane 1 is a molecular weight marker ($\phi$X174/HaeIII), Lane 2 is the positive control, Lane 3 is a result of the case when a single cell was the target, and Lane 4 is a result of the case when two cells were the target.

PCR method was performed using human β-globulin specific primer (primer 1:5'-GAAGAGCCAAGGACAGGTAC-3', primer2:5'-GGAAAATAGACCAATAGGCAG-3') on the DNA that was obtained using the above-described operations. The reaction was performed through a standard protocol. The first cycle of PCR was performed for five minutes at 94° C., two minutes at 41° C., and three minutes at 72° C. Successively, 30 more cycles were carried out for one minute at 94° C., five minutes at 53° C., and three minutes at 72° C. Then, the final cycle was performed for three minutes at 72° C. DNA fragments were obtained for the subject by performing PCR reaction using the same primer under the same conditions on genome DNA extracted from a HuL-1 cell. The obtained products and the subject DNA fragments were subjected to electrophoresis using 2.5% agarose gel. An image showing the results of the electrophoresis is shown in FIG. 3. Lane 1 is φX174/HaeIII DNA size markers that migrated as a molecular weight marker, lane 2 is the positive control, lane 3 is DNA product obtained when the target was a single cell, and lane 4 is DNA product obtained when the target was two cells. It can be seen from FIG. 3 that only specific cell(s) can be collected according to the method of the present invention, that DNA from the collected cell(s) can be obtained, and further that the DNA can be amplified using the PCR method.

Further, by using the DNA obtained through the above-described operations, the target DNA can be amplified by selecting an appropriate specific primer used in the PCR method. Genetic diagnosis can be performed using the amplified DNA.

SECOND EXAMPLE

Separation Method Using Amphoteric Photoresist

The method of a second example is schematically shown in FIGS. 4(a) to 4(f).

(2-1) Fix Cells Using Photoresist

Figure 4:
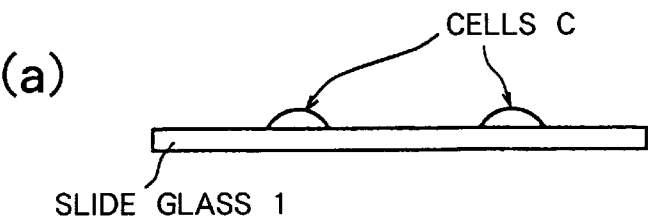
FIGS. 4(a) to 4(f) schematically show processes of a second example of the present invention.
Figure 4:
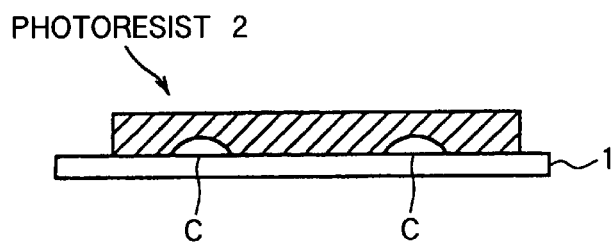
Figure 4:
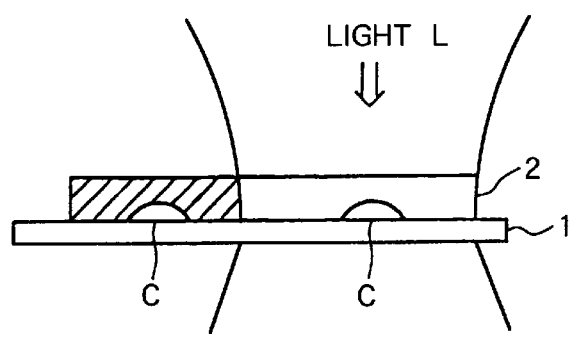
Figure 4:
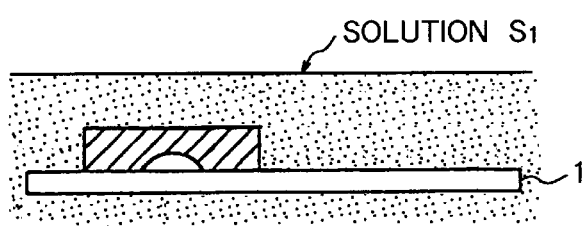
Figure 4:
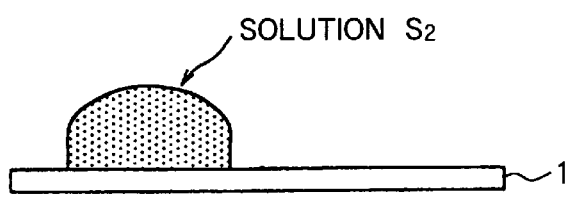
Figure 4:
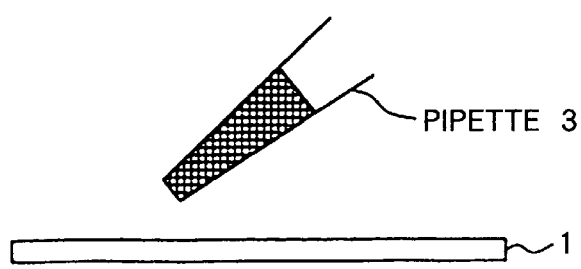

In the same manner as per 1-1 of the first example, cells C were prepared by cultivation in a single layer on a slide glass 1 as shown in FIG. 4(a). It should be noted that the photoresist SPR6112 used in the first example also serves as an amphoteric photoresist.

After 300μ 1 of photoresist 2 (SPR6112 produced by Shipley Co.) was added onto the slide glass 1, the slide glass 1 was heated for several minutes at 95° C. to solidify the photoresist 2 as shown in FIG. 4(b). The layer of the solidified photoresist 2 was approximately 7 μm thick. It was confirmed that the cells C can be stored in this condition for a month or more.

(2-2) Collection of Target Cell

The obtained sample was transferred to under a fluorescence microscope (Axioplan model produced by Carl Zweiss), the cells were observed using differential interference techniques, and a target cell was determined.

Next, as shown in FIG. 4(c), the area of the photoresist other than the portion thereof that includes the target cell was irradiated for about 10 seconds with 440 nm wavelength light L using a high pressure mercury lamp.

A first solution Si was prepared by adding Tween 20 to 0.1N of sodium hydroxide solution to obtain a 0.5%(v/v) concentration of Tween 20. After irradiation, as shown in FIG. 4(d), the slide glass was immersed in the first solution S1 and left to sit for about 8 to 10 minutes at room temperature to dissolve (develop) the photoresist 2 and remove the irradiated portion.

As shown in FIG. 4(e), 10 μl of xylene (second solution S2) was added to dissolve the remaining portion of the photoresist 2. As shown in FIG. 4(f), the target cell was collected.

(2-3) Extraction and Amplification of DNA from Collected Cell

DNA was collected and amplified using the PCR method in the same manner as per operation (1-3) of the first example, and an obtained PCR product was subjected to electrophoresis. As a result, the PCR product was confirmed as similar to that obtained in the first example.

THIRD EXAMPLE

Separation Method Using Negative Photoresist

A method of a third example is schematically shown in FIGS. 5(a) to 5(e).

(3-1) Collection of Target Cell

Figure 5:
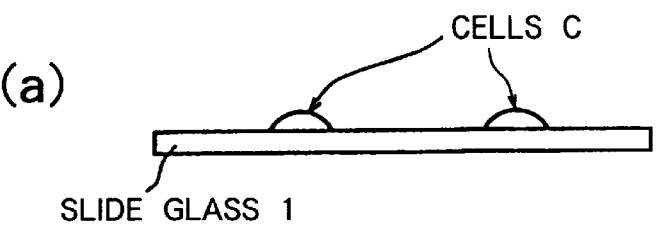
FIGS. 5(a) to 5(e) schematically show processes of a third example of the present invention.
Figure 5:
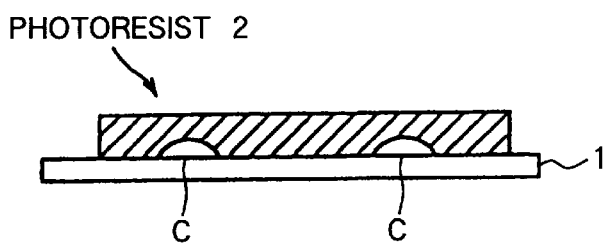
Figure 5:
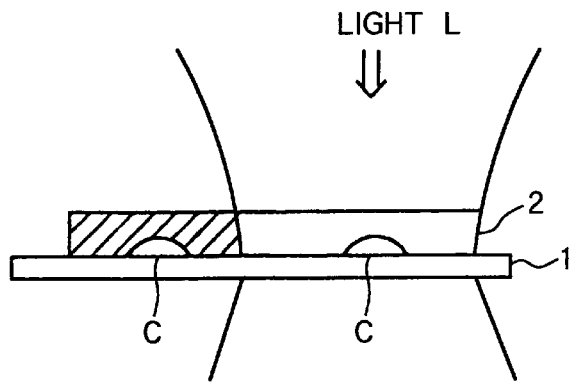
Figure 5:
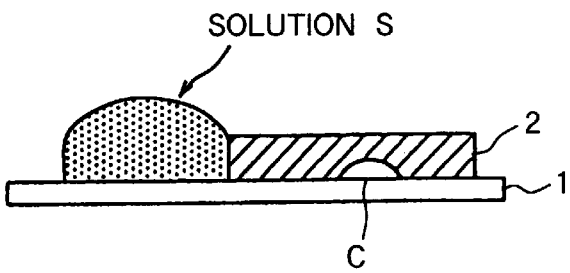
Figure 5:
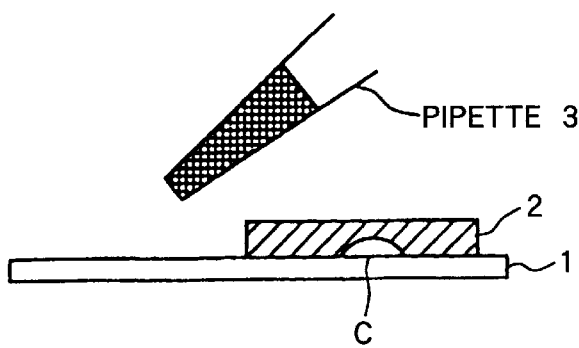

In the same manner as per 1-1 of the first example, cells C were prepared by cultivation in a single layer on a slide glass 1 as shown in FIG. 5(a).

300 μl of photoresist 2 (Model OMR85 produced by Tokyo Ohka Kogyo Co., Ltd.) was added onto the slide glass 1, and the photoresist 2 was solidified in the same manner as per 1-1 of the first example.

The cells covered with the photoresist was transferred to under a fluorescence microscope (Axioplan model produced by Carl Zweiss), the cells were observed using differential interference techniques, and a target cell was determined.

Next, the area of the photoresist other than the portion thereof that includes the target cell was irradiated for about 10 seconds with 440 nm wavelength light L using a high pressure mercury lamp as shown in FIG. 5(c).

As shown in FIG. 5(d), 10 μl of xylene (solution S) was added to the unirradiated portion of the photoresist to dissolve the photoresist. As shown in FIG. 5(e), the target cell was collected.

(3-2) Extracting and Amplifying DNA from Collected Cell

DNA was collected and amplified using the PCR method in the same manner as per (1-3) of the first example. Afterward, the obtained PCR product was subjected to electrophoresis. As a result, the PCR product was confirmed as similar to that obtained in the first example.

FOURTH EXAMPLE

Figure 6:
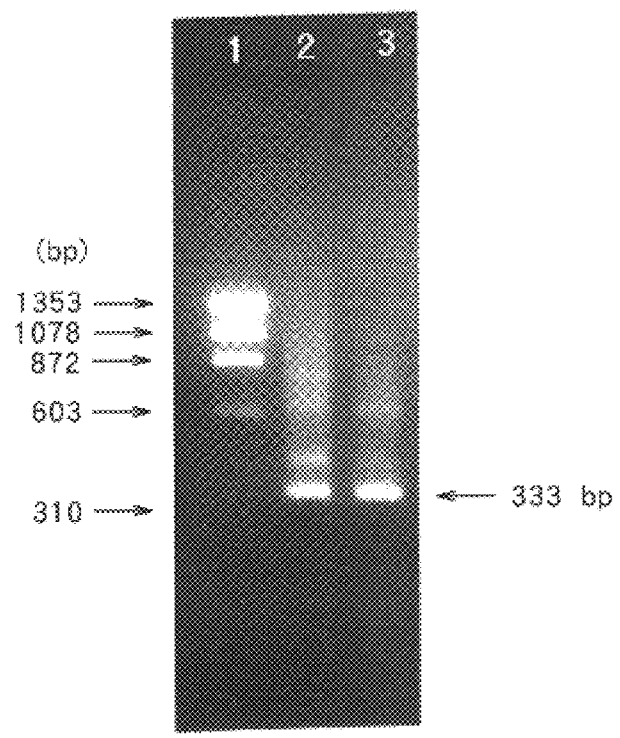
FIG. 6 is an electrophoretic pattern of PCR products obtained during a process of a fourth example using p53 specific primer, wherein Lane 1 is a molecular weight marker ($\phi$X174/HaeIII), Lane 2 is the subject, and Lane 3 is a result of the case when 50 cells were the target.

Separation Method Using Positive Photoresist (2)—Considerations With Respect to Suspended Cells NIH/3T3 cells derived from mouse were cultivated in a DMEM (10% addition fetal bovine serum) culture medium in a culture Petri dish at 37° C. and in a 5% $CO_2$ atmosphere. Next, the cells were subjected to trypsinization to prepare suspended cells. The cells were washed two times in PBS. Then, a cell suspension was prepared by adjusting the cell count to $5\times10^5$ cells/ml. Next, 10 μl of the cell suspension was added to 90 μl of positive photoresist liquid (SPR6112 produced by Shipley Co.) and mixed by lightly pipetting the two liquids. Afterward, the mixture was added to a slide glass and the mixture was spread by tilting the slide glass. The photoresist was formed into a layer by heating for 30 minutes at 45° C. In the same manner as in the first example, the obtained sample was irradiated under a fluorescence microscope with 440 nm light for 50 cells as the target. After irradiation, a solution made from 10 μl of 0.1N NaOH and 20% of Tween 20 was added to the irradiated portion and left at room temperature for 7 minutes to dissolve the resist. The dissolved liquid was collected using a pipette. Next, 17 μl of distilled water was added to the collected liquid. Further, 3 μl of 3M sodium acetate solution (pH 5.2) was added. Then, 75 μl of cold ethanol was added and the mixture was thoroughly agitated. The obtained liquid was placed for one hour in a refrigerator at −20° C. and then centrifuged in a microtube centrifuge at 15,000 rpm for one hour. The precipitate was collected, washed once in 70% ethanol, and dried. Protease K was added to the precipitate until a final concentration of 100 μg/ml was attained. Then, 1×PCR buffer was prepared in a final volume of 20 μl. The obtained solution was reacted at 55° C. for one hour to digest the protein in the system. After reaction was completed, the solution was heated for 10 minutes at 95° C. to arrest enzyme activity. PCR was performed on the obtained DNA liquid by using a primer (primer 1:5'CTGTGCAGTTGTGGGTCAGA-3', primer 2:5'-AAAGATAGGTCGGCGGTTCAT-3') specific to p53. Taq polymerase produced by Boehringer-Mannheim Co. was used in the PCR procedure. The reactant solution was composed according to the protocol included with the Taq polymerase. The temperature conditions for the reaction were first 95° C. for five minutes and 59° C. for five minutes. Then, 30 temperature cycles of 72° C. for 1.5 minutes, 94° C. for 45 seconds, and 59° C. for one minute were repeated. The final cycle was performed at 72° C. for ten minutes. The subject was DNA fragments obtained by performing PCR reactions using the same primer and under the same conditions on genome DNA extracted from a NIH/3T3 cell following "PCR PROTOCOLS," M. A. Innis et al (Academic Press, 1990, pages 146 to 152). The obtained product and the subject DNA fragments were subjected to electrophoresis using a 2.5% agarose gel. The results of the electrophoresis are shown in FIG. 6. In lane 1, φX174/HaeIII DNA size markers migrated as a molecular weight marker, lane 2 is the subject, and lane 3 is DNA product obtained according to the present example. It can be seen from FIG. 6 that the method of the present invention can be used to collect specific cells only, that DNA can be obtained from the collected cells, and that the DNA can be amplified using PCR method.

According to the above-described examples, mRNA can be collected and amplified using the RT-PCR method instead of the PCR method.

Only a portion of the photoresist that covers a certain position of a chromosome can be exposed by using laser light. Accordingly, it is possible to collect and amplify only a region of DNA at a certain position of a chromosome.

The present invention is not limited to the above-described embodiments and can be modified in a variety of ways within the scope disclosed in the claims. For example, in the method using amphoteric photoresist, the photoresist is exposed to light at its portions other than the portion covering the portion of the biological sample that includes the target biological substance to be collected. Then, a first solvent (a weak alkaline solution in this case) is used to remove the exposed portions. Afterward, a second solvent (an organic solvent such as xylene) is used to collect the unexposed portions. However, the following processes can be employed using a combination of other solvents. That is, first, the photoresist is exposed to light at a portion covering the portion of the biological sample that includes the target biological substance to be collected. Then, the unexposed portion is removed using a first solvent and afterward the exposed portion is collected using a second solvent. In this way, by utilizing the difference in solubility to solvent between exposed and unexposed portions of the amphoteric photoresist, either the portion covering the target to be collected can be exposed to light or the portion not covering the target to be collected can be exposed to light according to combinations of a variety of solvents.

INDUSTRIAL APPLICABILITY

As described above, the method according to the present invention is useful because a particular biological substance, such as cells, tissues, biopolymers, or low weight biomolecules, for example, DNA, RNA, protein, or glucose, can be selectively separated from the surrounding portion by using simple operations and without impurities from the surrounding portion being mixed therein.

Further, the biological substance, such as DNA, RNA, protein, or glucose, collected using the method of the present invention is useful because it can be used for genetic cloning, for preparing a cDNA library, for genetic diagnosis, for amino acid sequencing, for biological diagnosis, and the like.

Further, the biological sample embedded in photoresist according to the present invention is useful because it can be preserved.

What is claimed is:

1. A method for separating a biological substance from a biological sample, the method comprising the steps of:
   (a) covering, with a photoresist, a biological sample that includes a biological substance to be collected;
   (b) fixing the biological sample by solidifying the photoresist;
   (c) selectively exposing the solidified photoresist to light either at a portion that covers the biological substance or at another portion;
   (d) selectively dissolving, using a solvent, at least one of the portion of the photoresist that is exposed to light during the step (c) and the portion that is not exposed to light; and
   (e) collecting the biological substance embedded in the photoresist to thereby separate the biological substance from the biological sample.

2. A method for separating a biological substance as claimed in claim 1, wherein the photoresist is a positive type photoresist.

3. A method for separating a biological substance as claimed in claim 1, wherein the photoresist is a negative type photoresist.

4. A method for separating a biological substance from a biological sample, the method comprising the steps of:
   (a) covering, with a positive type photoresist, a biological sample that includes a biological substance;
   (b) fixing the biological sample by solidifying the photoresist;
   (c) exposing the solidified photoresist to light at a portion that covers the biological substance;
   (d) dissolving, using a solvent, the portion of the photoresist that is exposed to light during the step (c); and
   (e) collecting the biological substance embedded in the photoresist to thereby separate the biological substance from the biological sample.

5. A method for separating a biological substance as claimed in claim 4, wherein the exposure step (c) includes irradiation of the photoresist with at least one selected from the group consisting of visible light, ultraviolet light, X-rays, and an electron beam.

6. A method for separating a biological substance as claimed in claim 4, wherein the positive photoresist is selected from the group consisting of a photoinduced chemical property changing type photoresist and a photodegradation type photoresist.

7. A method for separating a biological substance as claimed in any of claim 4, wherein the step (b) of solidifying the photoresist is performed by heating the photoresist at a temperature between room temperature and 100° C.

8. A method for separating a biological substance from a biological sample, the method comprising the steps of:
   (a) covering, with a negative type photoresist, a biological sample that includes a biological substance;
   (b) fixing the biological sample by solidifying the photoresist;
   (c) exposing, to light, a portion of the photoresist that covers a region other than a portion of the biological sample including the biological substance to be collected, thereby making the photoresist at the exposed portion insoluble with respect to a solvent; and
   (d) collecting the biological substance covered by the unexposed portion of the photoresist, which is not made insoluble with respect to the solvent to thereby separate the biological substance from the biological sample.

9. A method for separating a biological substance as claimed in claim 8, wherein the exposure step (c) includes irradiation of the photoresist with at least one selected from the group consisting of visible light, ultraviolet light, X-rays, and an electron beam.

10. A method for separating a biological substance as claimed in claim 8, wherein the negative type photoresist is either an optical cross-linking photoresist that generates a cross-linking reaction upon irradiation with light, X rays, or an electron beam, or a photo polymerized resist that includes a radical generating agent and that polymerizes when exposed to light.

11. A method using a method of claim 1 to separate at least one selected from the group consisting of DNA, RNA, proteins, and low weight biomolecules from a biological sample.

12. A method for separating a biological substance as claimed in claim 1, wherein the collecting step (e) collects the biological substance embedded in a portion of the photoresist that is dissolved during the dissolving step (d).

13. A method for separating a biological substance as claimed in claim 12, wherein the collecting step (e) includes the steps of:
   collecting the portion of the photoresist that is dissolved during the dissolving step (d) and that is embedded with the biological substance; and
   separating the biological substance from the collected, dissolved portion of the photoresist.

14. A method for separating a biological substance as claimed in claim 4, wherein the collecting step (e) collects the biological substance embedded in a portion of the photoresist that is dissolved during the dissolving step (d).

15. A method for separating a biological substance as claimed in claim 14, wherein the collecting step (e) includes the steps of:
   collecting the portion of the photoresist that is dissolved during the dissolving step (d) and that is embedded with the biological substance; and
   separating the biological substance from the collected, dissolved portion of the photoresist.

16. A method for separating a biological substance as claimed in claim 12, wherein the exposure step (c) exposes the solidified photoresist to light at the portion other than the portion that covers the biological substance to be collected, and
   wherein the dissolving step (d) includes:
      a first dissolving step of dissolving, using a solvent, the exposed portion of the photoresist; and
      a second dissolving step of dissolving, using another solvent, a remaining unexposed portion of the photoresist; and
      wherein the collecting step (e) collects the biological substance embedded in the unexposed portion of the photoresist that is dissolved during the second dissolving step.

17. A method for separating a biological substance as claimed in claim 16, wherein the collecting step (e) further includes the steps of:
   collecting the portion of the photoresist that is dissolved during the second dissolving step and that is embedded with the biological substance; and
   separating the biological substance from the collected, dissolved portion of the photoresist.

18. A method for separating a biological substance as claimed in claim 8, wherein the collecting step (d) includes the steps of:

dissolving the unexposed portion of the photoresist; and collecting the biological substance embedded in the dissolved portion of the photoresist.

19. A method for separating a biological substance as claimed in claim 18, wherein the collecting step (d) further includes the steps of:

collecting the portion of the photoresist that is dissolved during the dissolving step and that is embedded with the biological substance; and separating the biological substance from the collected, dissolved portion of the photoresist.

20. A method for separating a biological substance as claimed in claim 7, wherein the temperature is between 30° C. and 100° C.

21. A method for separating a biological substance as claimed in claim 12, wherein the exposure step (c) exposes the solidified photoresist to light at the portion that covers the biological substance to be collected, and wherein the dissolving step (d) dissolves, using a solvent, the portion of the photoresist that is exposed to light during the step (c).

22. A method for separating a biological substance as claimed in claim 12, wherein the exposure step (c) exposes the solidified photoresist to light at the portion other than the portion that covers the biological substance to be collected, and wherein the dissolving step (d) dissolves, using a solvent, the portion of the photoresist that is not exposed to light during the step (c).

* * * * *